United States Patent [19]

Lachmann et al.

[11] 4,140,673
[45] Feb. 20, 1979

[54] PIPERIDINE DERIVATIVES AS LIGHT STABILIZERS

[75] Inventors: Burkhard Lachmann, Meerbusch-Buederich; Hans J. Rosenkranz, Krefeld; Harald Oertel, Odenthal-Gloebusch; Alfred Pischtschan, Kuerten-Eichhof; Aziz El-Sayed, Leverkusen, all of Fed. Rep. of Germany

[73] Assignee: Bayer Aktiengesellschaft, Fed. Rep. of Germany

[21] Appl. No.: 778,714

[22] Filed: Mar. 17, 1977

[30] Foreign Application Priority Data

Mar. 23, 1976 [DE] Fed. Rep. of Germany ....... 2612314

[51] Int. Cl.² .................. C07D 211/58; C07D 401/12; C08K 5/34
[52] U.S. Cl. ................. 260/45.8 N; 260/45.7 PH; 260/45.8 NT; 260/77.5 SS; 546/186; 546/223; 542/424
[58] Field of Search ............. 260/45.8 N, 293.63, 260/293.87; 542/424

[56] References Cited

U.S. PATENT DOCUMENTS

| | | | |
|---|---|---|---|
| 3,503,982 | 3/1970 | Murayama et al. | 260/45.8 N |
| 3,534,048 | 10/1970 | Murayama et al. | 260/45.8 N |
| 3,573,216 | 3/1971 | Strobel et al. | 260/45.8 N |
| 3,684,765 | 8/1972 | Matsui et al. | 260/293.87 |
| 3,705,166 | 12/1972 | Murayama et al. | 260/293.87 |
| 3,734,883 | 5/1973 | Holt | 260/293.63 |
| 3,887,517 | 6/1975 | Murayama et al. | 260/45.8 N |
| 3,904,581 | 9/1975 | Murayama et al. | 260/45.8 N |
| 3,984,371 | 10/1976 | Murayama et al. | 260/45.8 N |
| 4,046,736 | 9/1977 | Hardy | 260/293.63 |
| 4,088,629 | 5/1978 | Uhrhan et al. | 260/293.63 |

Primary Examiner—Melvyn I. Marquis
Assistant Examiner—R. A. White
Attorney, Agent, or Firm—Connolly and Hutz

[57] ABSTRACT

Piperidine derivatives of formula

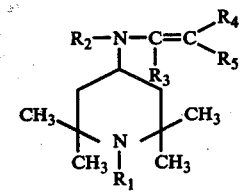

can be prepared by reacting 4-amino-piperidine with for example enolic ethers. The compounds obtained may be used as stabilizers.

10 Claims, No Drawings

PIPERIDINE DERIVATIVES AS LIGHT STABILIZERS

This invention relates to new piperidine derivatives and to their use as stabilisers for polymers. The new compounds correspond to the general formula:

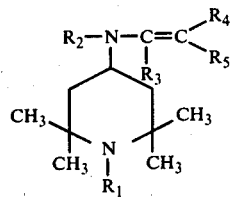

in which
R$_1$ represents H or a methyl radical,
R$_2$ represents H, a straight-chain or branched alkyl radical with 1 to 8 carbon atoms, a cycloalkyl radical with 5 to 8 carbon atoms, an aralkyl radical with 7 to 12 carbon atoms, a β-cyanoethyl radical, a β-alkoxycarbonyl ethyl radical with 1 to 3 carbon atoms in the alkoxy moiety, a phenyl radical which may optionally be substituted by straight chain or branched alkyl radicals with 1 to 4 carbon atoms, halogen or the methoxy group, or formula (II):

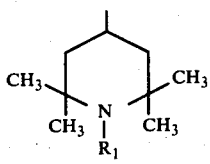

in which
R$_1$ represents H or a methyl radical, R$_3$ represents H, a straight-chain or branched alkyl radical with 1 to 4 carbon atoms, a phenyl radical which may optionally be substituted by straight-chain or branched alkyl radicals with 1 to 4 carbon atoms, halogen or the methoxy group, R$_4$ represents CN; —COOR$_6$;

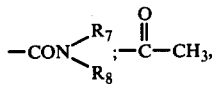

R$_5$ represents R$_4$, a phenyl radical which may optionally be substituted by straight-chain or branched alkyl radicals with 1 to 4 carbon atoms, halogen or the methoxy group,
R$_6$ represents a straight-chain or branched alkyl radical with 1 to 12 L carbon atoms or a cycloalkyl radical with 5 to 8 carbon atoms, and
R$_7$ and R$_8$ are the same or independently of one another represent H, a straight-chain or branched alkyl radical with 1 to 12 carbon atoms, a cycloalkyl radical with 5 to 8 carbon atoms, or formula (II) in which R$_1$ may represent H or a methyl radical.

The preferred radical for R$_1$ is hydrogen.
Examples of R$_2$ include H, methyl, ethyl, n-propyl, isopropyl, n-butyl, sec.-butyl n-hexyl, n-octyl, cyclohexyl, benzyl, β-cyanoethyl, β-methoxycarbonylethyl, phenyl, p-methyl phenyl, p-methoxyphenyl and 2,2,6,6-tetramethyl-4-peperidinyl, but preferably H, an alkyl radical with 1 to 4 carbon atoms, cyclohexyl, benzyl or phenyl.

Examples of R$_3$ are H, methyl, ethyl, propyl, phenyl and p-methylphenyl, but preferably H, methyl or phenyl.

Examples of R$_4$ and R$_5$ are CN, methoxycarbonyl, ethoxy carbonyl, n-butoxycarbonyl, isopropoxycarbonyl, n-octoxycarbonyl, acetyl, phenyl, p-chlorophenyl, p-methylphenyl, cyclohexyloxy-carbonyl, aminocarbonyl, dimethylaminocarbonyl, ethanolamino-carbonyl, diethanolaminocarbonyl, n-butylaminocarbonyl, isopropanolaminocarbonyl, cyclohexyl-aminocarbonyl and N-(2,2,6,6-tetramethyl-4-piperidinyl)aminocarbonyl radicals, but preferably CN, methoxycarbonyl, ethoxycarbonyl, cyclohexyloxy-carbonyl, n-octyloxycarbonyl, acetyl or phenyl radicals.

Examples of R$_6$ are methyl, ethyl, propyl, isopropyl, n-butyl, isobutyl, hexyl, cyclohexyl, n-octyl and dodecyl radicals, but preferably methyl, ethyl, n-butyl, or n-octyl radicals.

Examples of R$_7$ and R$_8$ are H, methyl, ethyl, propyl, n-butyl, hydroxyethyl, 2-hydroxypropyl, n-hexyl, cyclohexyl, decyl and the 2,2,6,6-tetramethyl-4-piperidinyl radical.

The following compounds are mentioned as examples of compounds corresponding to the general formula (I):

TABLE I

α-cyano-β-[N-(2,2,6,6-tetramethyl-4-piperidinyl)]-aminoacrylic acid methyl ester
α-cyano-β-[N-(2,2,6,6-tetramethyl-4-piperidinyl)]-aminoacrylic acid ethyl ester
α-cyano-β-[N-(2,2,6,6-tetramethyl-4-piperidinyl)]-aminoacrylic acid-n-butyl ester
α-cyano-β-[N-(2,2,6,6-tetramethyl-4-piperidinyl)]-aminoacrylic acid-n-octyl ester
α-cyano-β-methyl-β-[N-(2,2,6,6-tetramethyl-4-piperidinyl)]-amino-acrylic acid methyl ester
α-cyano-β-phenyl-β-[N-(2,2,6,6-tetramethyl-4-piperidinyl)]-aminoacrylic acid methyl ester
α-cyano-β-[N,N-bis-(2,2,6,6-tetramethyl-4-piperidinyl)]-aminoacrylic acid methyl ester
α-ethoxycarbonyl-β-[N-phenyl-N-(2,2,6,6-tetramethyl-4-piperidinyl)]-aminoacrylic acid ethyl ester
α-cyano-β-[N-(p-methylphenyl)-N-(2,2,6,6-tetramethyl-4-piperidinyl)]-aminoacrylic acid methyl ester
α-phenyl-β-[N-(2,2,6,6-tetramethyl-4-piperidinyl)]-aminoacrylic acid methyl ester
N-(2,2,6,6-tetramethyl-4-piperidinyl)-aminomethylene acetyl acetone
α-cyano-β-[N-methyl-N-(2,2,6,6-tetramethyl-4-piperidinyl)]-aminoacrylic acid methyl ester
α-cyano-β-[N-n-butyl-N-(2,2,6,6-tetramethyl-4-piperidinyl)]-aminoacrylic acid methyl ester
α-cyano-β-[(N-cyclohexyl-N-(2,2,6,6-tetramethyl-4-piperidinyl)]-aminoacrylic acid methyl ester
α-acetyl-β-[N-(2,2,6,6-tetramethyl-4-piperidinyl)]-aminoacrylic acid ethyl ester
α-methoxycarbonyl-β-[N-(2,2,6,6-tetramethyl-4-piperidinyl)]-aminoacrylic acid methyl ester
α-ethoxycarbonyl-β-[N-(2,2,6,6-tetramethyl-4-piperidinyl)]-aminoacrylic acid ethyl ester
α-ethanolaminocarbonyl-β-[N-(2,2,6,6-tetramethyl-4-piperidinyl)]-aminoacrylonitrile
α-diethanolaminocarbonyl-β-[N-(2,2,6,6-tetramethyl-4-piperidinyl)]aminoacrylonitrile α-n-butylaminocarbonyl-β-[N-(2,2,6,6-tetramethyl-4-piperidinyl)]-aminoacrylonitrile α-[N-(2,2,6,6-tetramethyl-4-piperidinyl)]-aminocarbonyl-β-[N-(2,2,6,6-tetramethyl-4-piperidinyl)]-aminoacrylonitrile α-cyano-β-[N-(2,2,6,6-tetramethyl-4-piperidinyl)]-amino-acrylonitrile α-cyano-β-methyl-β-[N-(2,2,6,6-tetramethyl-4-piperidinyl)]-aminoacrylonitrile α-cyano-β-[N-methyl-N-(2,2,6,6-tetramethyl-4-piperidinyl)]-aminoacrylonitrile α-phenyl-β-[N-(2,2,6,6-tetramethyl-4-piperidinyl)]-aminoacrylonitrile.

The compounds of the general formula (I) are obtained for example by condensing compounds corresponding to the general formula (III) with compounds of the general formula (IV):

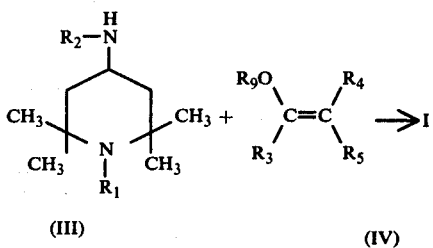

(III)     (IV)

The radicals $R_1$, $R_2$, $R_3$, $R_4$ and $R_5$ have the meanings defined above. $R_9$ represents H or a $C_1$–$C_4$-alkyl radical, preferably methyl or ethyl.

In general, one equivalent of a compound of the general formula (III) may be reacted with from 0.5 to 1.5 equivalents and preferably with from 0.8 to 1.2 equivalents of a compound of the general formula (IV), the reaction generally taking place in a suitable solvent which is inert to the reactants.

The process is carried out at temperatures in the range of from 0° to 100° C., preferably at temperatures in the range of from 10° to 60° C. and, with particular preference, at temperatures in the range of from 20° to 50° C.

Suitable solvents are, for example, chloroform, methylene chloride, toluene, chlorobenzene, cyclohexane, acetone, methylethyl ketone, methanol, ethanol, isopropanol, isobutanol, acetonitrile and water. It is also possible to use mixtures of two or more solvents. The solvent volume is advantageously selected in such a way that the reaction mixture remains readily stirrable. It is preferred to use from 2 to 10 parts by weight of solvent per part by weight of the compound of general formula (III).

The reaction time may be between 1 and 15 hours and is preferably between 3 and 10 hours.

The reaction product is generally worked up by the usual methods, namely filtration of the reaction product which has crystallised out or fractionation of the reaction solution.

The invention also relates to the use of the compounds of general formula (I) as stabilisers against the degradation of polymers by photooxidation. The invention also relates to the polymers stabilised with the compounds of general formula (I).

The following polymers are mentioned by way of example: polystyrenes, polyurethanes, polyacrylonitriles, polyacrylates, polymethacrylates and copolymers thereof; polymers of the acrylonitrile-butadiene-styrenetype and of the acrylonitrile-ethylene-styrene type; polyolefins such as, for example, polybutadiene, polyvinyl chloride, polyvinylidene chloride, polyethylene, polypropylene and copolymers thereof; polyethers, polycarbonates; plastics materials based on cellulose such as, for example, cellulose acetate or cellulose butyrate; polyesters based on α,β-ethylenically unsaturated dicarboxylic acids and polyols, especially glycols, for example those of maleic acid anhydride and propylene glycol; saturated polyesters based on adipic acid, terephthalic acid, ethylene glycol, 1,6-hexane diol or 1,2-propane diol; and polyamides based on ε-caprolactam or condensates of hexamethylene diamine and adipic acid.

One important group of polymers to be stabilised are the acrylonitrile-butadiene-styrene and the and the acrylonitrile-ethylene styrene copolymers and graft polymers.

Another important group of polymers to be stabilised are the elastic polyurethanes which may optionally be present in the foamed form and which may be produced by methods known per se from the known starting materials. The polyurethanes are generally obtained by reacting relatively high molecular weight polyhydroxyl compounds (for example polyesters or polyethers with a molecular weight of from about 500 to 5000 and with melting points of preferably below 60° C. and aliphatic, araliphatic or aromatic polyisocyanates (preferably aromatic diisocyanates, such as tolyene diisocyanate or diphenyl methane-4,4'-diisocyanate) and so-called chain extenders, i.e. low molecular weight compounds having molecular weights for example of 18 to 400) containing two or more isocyanate-reactive groups (for example water, low molecular weight diols, diamines, dihydrazides or similar compounds such as, for example, amino-alcohols, aminohydrazides hydroxy hydrazides amino-semicarbazides, semicarbazide hydrazides, semicarbazide carbazinic esters or corresponding mixtures of these chain extenders, in single stage or multistage processes, either in the melt or in solvents, by any one of a number of known and modifiable processes.

The following are mentioned as examples of suitable starting materials for the polyurethanes: polyesters of adipic acid and dialcohols with from 2 to about 10 carbon atoms, preferably those containing more than 5 carbon atoms, the dialcohols also being usuable in admixture to lower the melting points of the polyesters; polyesters of caprolactone and dialcohols, also polyalkylene ether diols, especially polytetramethylene ether diols, poly-trimethylene ether diols, polypropylene glycol or corresponding copolyethers. Preferred diisocyanates are aromatic diisocyanates, such as diphenyl methane-4,4'-diisocyanate, tolylene diisocyanate, araliphatic diisocyanates such as m-xylylene diisocyanate or even aliphatic diisocyanates, such as hexamethylene diisocyanate materials are reacted, optionally together with dialcohols, to form NCO-preadducts which preferably have the structures defined in Belgium Patent No. 734,194. Suitable chain extenders, which may optionally be used in admixture or in a multistage reaction, are water and/or trialcohols, such as butane diol and p-xylylene glycols, trimethylol propane, aminoalcohols such as ethanolamine, diamines such as diphenyl methane-4,4'-diamine, 3,3'-dichlorodiphenyl methane-4,4'-diamine, but preferably aliphatic diamines such as ethylene diamine, 1,1-propylene diamine, isophorone diamine, meta-xylylene diamine and also hydrazine or dihydrazides, such as carbodihydrazide, oxalic acid dihydrazide, glutaric acid dihydrazide, pimellic acid dihydrazide, terephthalic acid dihydrazide, β-alanyl hydrazide or semicarbazide hydrazides, such as β-semicarbazide alkyl hydrazide, optionally in the form of mixtures of the chain extenders. It is preferred to stabilise polyurethanes which, in addition to urethane groups, also contain —NH-CO-NH-groups formed by the reaction of isocyanate groups with water and/or compounds containing terminal NH$_2$-groups (for example diamines, dihydrazides, carbodihydrazide, semicarbazide hydrazides or hydrazine) and which have a substantially linear, segmented molecular structure, are soluble in highly polar solvents, such as dimethyl formamide or dimethyl acetamide, before they are shaped and whose characteristic segments may be characterised by the following formula:

This segment may be formed from the reaction of an NCO-preadduct CON-Y.NCO with a chain extender H$_2$N.X.NH$_2$.

The radical —Y— of the NCO-preadduct may have the following structure, for example:

or other standard compositions (cf. Belgian Pat. No. 734,104).

In the above formula, R represents a difunctional aliphatic, araliphatic or aromatic radical (of a diisocyanate), D represents the radical of a relatively high molecular weight polyhydroxyl compound with a molecular weight of from 500 to 5000 and with melting points below 60° C. without its terminal hydroxyl groups (for example the radical of a polyalkylene ether, polyester or polyacetal poly-N-alkyl urethane). X represents the radical of a difunctional chain extender having termanal NH$_2$-groups but without the terminal NH$_2$- groups, for example an aliphatic, araliphatic, aromatic or heterocyclic radical, an —HN-CO-alkylene-CO-NH— radical, an —NH-CO-NH-(CH$_2$)$_2$-CO-NH-radical or a bond between two nitrogen atoms. The synthesis of polyurethane (ureas) of this type is described in detail, for example in German Auslegeschrift No. 1,270,276 and in Belgian Pat. No. 734,194. Polyurethane foams may be produced for example with addition of the stabilisers to the starting components (for example polyethers) by known methods and recipes (cf. for example Kunststoff-Handbuch, Vol. VII, Polyurethane, Carl Hanser Verlag Munich, 1966, pages 440 to 457, 504 and 531).

The polymers are degraded under the effect of UV-light, oxygen and/or heat. This degradation is reflected in yellowing and/or in a deterioration of mechanical properties such as, for example, notched impact strength, tensile strength and flexural strength. For protection against this degradation by light, oxygen and/or heat, the polymers are stabilised with UV-absorbers or light stabilisers. One of the results of the development of plastics materials with increasingly better properties is that the light stabilisers to be incorporated also have to satisfy increasingly more stringent requirements. Unfortunately, the stabilisers hitherto commercially available for stabilising these polymers, such as for example benzophenone compounds, derivatives of benztriazole or phenol derivatives, do not satisfy all the requirements made of them.

It has now been found that the compounds of general formula (I) according to the invention provide polymers with excellent protection against degradation by photooxidation. The compounds of general formula (I) according to the invention are distinguished from other 2,2,6,6-tetrasubstituted piperidine derivatives, of the type described, for example, in German Offenlegungsschrifts Nos. 2,349,962 and 2,402,636, by the fact that they absorb UV-light to the region of 300 mm with high extinction.

By way of illustration, the UV-absorption values and associated molar extinction coefficients ε of some typical representatives of the compounds according to the invention are shown in Table 2.

Table 2

$$R_2-N-C=C\begin{smallmatrix}R_4\\R_5\end{smallmatrix}$$

with piperidine ring bearing R$_3$, CH$_3$, CH$_3$, N-R$_1$, CH$_3$, CH$_3$

| Compound | R$_1$ | R$_2$ | R$_3$ | R$_4$ | R$_5$ | m.p. °C | λmax (nm) | ε |
|---|---|---|---|---|---|---|---|---|
| I | H | H | H | CN | COOCH$_3$ | 162 | 285 | 25000 |
| II | H | H | H | CN | CN | 205 | 282 | 24000 |
| III | H | H | H | COOC$_2$H$_5$ | COOC$_2$H$_5$ | 52–54 | 285 | 26000 |
| IV | H | H | CH$_3$ | CN | COOCH$_3$ | 153 | 287 | 23500 |
| V | H | CH$_3$ | H | CN | CN | 157 | 284 | 23200 |
| VI | H | H | H | —C(=O)—CH$_3$ | C(=O)—CH$_3$ | 144 | 295 | 20000 |
| VII | H | H | H | —C(=O)—CH$_3$ | C(=O)—OC$_2$H$_5$ | 96 | 300 | 18000 |
| VIII | H | H | H | CN | phenyl | 148 | 295 / 315 | 17000 / 16600 |
| IX | H | H | H | CN | COOC$_8$H$_{17}$ | 111 | 286 | 23700 |
| X | | | | Trinuvin 770, a product of Ciba-Geigy, shows no absorption in the range from 230–400 nm, | | | | |

The compounds of the general formula (I) used as stabilisers in accordance with the invention may be incorporated by known methods, for example by:

1. Adding the stabiliser to the polymer melt in solid or molten form or in the form of a solution, suspension or emulsion.

2. Powdering or tumble-coating the stabiliser onto the solid plastics material (granulate), followed by extrusion at the melting temperature.
3. Addition to suspended or dissolved polymers during their processing.
4. Producing plastics combinations with high contents of stabiliser (master batches) and subsequently mixing these concentrates with unstabilised plastics material.

The quantity in which the stabiliser is used in accordance with the invention is determined by the type and special application of the polymer and may be selected at the descretion of the average expert. In general, the stabiliser is used in a quantity of from 0.01 to 5% by weight, preferably in a quantity of from 0.05 to 3.5% by weight and with particular preference in a quantity of from 0.05 to 2.5% by weight, based on the quantity of polymer.

In addition to the stabilisers according to the invention, other known additives may be worked into the polymer. Additives such as these include heat stabilisers, flameproofing agents or antistatic agents, antioxidants of the sterically hindered phenol type, such as for example 2,6-di-tert.-butyl-p-cresol; 4,4'-thiobis-(6-tert.-butyl-3-methylphenol); 2,2'-thiobis-(6-tert.-butyl-4-methylphenol); α,α'-bis-(2-hydroxy-3,5-dialkylphenol)-p-diisopropyl benzenes; α,α'-bis-(2-hydroxy-3,5-di-alkylphenyl)-m-diisopropyl benzenes; 2,2'-methylene-bis-(4-methyl-6-tert.-butyl-phenyl); 2,2'-methylene-bis-(4-methyl-6-cyclohexylphenyl); 1,1,3-tris-(5-tert.-butyl-4-hydroxy-2-methyl-phenyl)-butane; tetrakis-(3,5-di-tert.-butyl-4-hydroxyphenyl-propionyloxymethyl)-methane; and also compounds of divalent sulphur such as for example dilauryl thiodipropionate; compounds of trivalent phosphorus such as, for example, triphenyl phosphite, tris-(p-nonylphenyl)-phosphite and also UV-absorbers based on 2-(2'-hydroxyphenyl)-benzotriazole such as, for example, 2-(2'-hydroxy-5'-methylphenyl)-benzotriazole and 2-(3',5'-di-tert.-butyl-2'-hydroxyphenyl)-5-chlorobenzotriazole; or even UV-absorbers based on benzophenone, such as for example 2-hydroxy-4-octoxy benzophenones; 2',4'-di-tert.-butyl phenyl-3,5-di-tert.-butyl-4-hydroxy benzoate; cyanoacrylic acid esters such as, for example, α-cyano-β-methyl-β-(p-methoxyphenyl)-acrylate and other light stabilisers such as, for example, 2,2'-thiobis-(4-tert.-octylphenolate) or n-butylamine nickel.

The invention is illustrated by but by no means limited to the following Examples, in which the parts and percentages are by weight.

EXAMPLE 1

α-Cyano-β-[N-(2,2,6,6-tetramethyl-4-piperidinyl)]-aminoacrylic acid methyl ester A solution of 233 g (1.5 moles) of ethoxymethylene cyanoacrylic acid methyl ester in 1 liter of ethanol is added dropwise over a period of 2 hours at room temperature to a solution of 234 g (1.5 moles) of 2,2,6,6-tetramethyl-4-aminopiperidine in 1 liter of ethanol. After stirring for 4 hours at room temperature, the reaction product precipitated is filtered off under suction. Recrystallisation from toluene gives 277 g of white crystals. M.p.: 161° C.

Analysis: $C_{14}H_{23}N_3O_2$; Calculated: C 63.4, H 8.68, N 15.85; Observed: C 62.9 H 8.78, N 15.8.

EXAMPLE 2

α-Cyano-β-[N-2,2,6,6-tetramethyl-4-piperidinyl)]-aminoacrylonitrile 12.4 g (0.1 mole) of ethoxymethylene malonic acid dinitrile and 17 g (0.11 mole) of 2,2,6,6-tetramethyl-4-aminopiperidine were reacted in 120 cc of ethanol in the same way as described in Example 1. Recrystallisation from toluene gave 17.2 g of white crystals. M.p.: 205° C.

Analysis: $C_{13}H_{20}N_4$; Calculated: C 67.2, H 8.62, N 24.14; Observed: C 66.8, H 8.80, N 24.40.

EXAMPLE 3

α-Cyano-β-methyl-β-[N-(2,2,6,6-tetramethyl-4-piperidinyl)]-aminoacrylic acid methyl ester 17 g (0.1 mole) of α-cyano-β-methyl-β-ethoxy acrylic acid methyl ester and 17 g (0.11 mole) of 2,2,6,6-tetramethyl-4-aminopiperidine were reacted in the same way as described in Example 1.

Yield: 22 g of white needles. M.p.: 153° C. Analysis: $C_{15}H_{25}N_3O_2$; Calculated: C 64.5, H 8.96, N 15.05; Observed: C 64.6, H 9.26, N 15.1.

EXAMPLE 4

α-Cyano-β-[N-(2,2,6,6-tetramethyl-4-piperidinyl)]-aminoacrylic acid-n-octyl ester The above compound was produced as described in Example 1 from equivalent quantities of 2,2,6,6-tetramethyl-4-aminopiperidine and ethoxymethylene cyanoacetic acid-n-octyl ester. White crystals, m.p.: 111° C.

Analysis: $C_{21}H_{37}N_3O_2$; Calculated: C 69.38, H 10.26, N 11.56; Observed: C 68.8, H 9.74, N 11.7.

EXAMPLE 5

α-Ethoxycarbonyl-β-[N-(2,2,6,6-tetramethyl-4-piperidinyl)]-aminoacrylic acid ethyl ester This compound was produced as described in Example 1 from equivalent quantities of 2,2,6,6-tetramethyl-4-aminopiperidine and ethoxymethylene malonic acid diethyl ester. Colourless crystals, m.p.: 51°–54° C.

Analysis: $C_{17}H_{30}N_2O_4$; Calculated: C 62.58, H 9.20, N 8.59; Observed: C 62.0, H 9.09, N 8.40.

EXAMPLE 6

α-Cyano-N-methyl-β-[N-(2,2,6,6-tetramethyl-4-piperidinyl)]-aminoacrylonitrile

This compound was produced as described in Example 1 from equivalent quantities of 2,2,6,6-tetramethyl-4-methylaminopiperidine and ethoxymethylene malodinitrile. Pale yellow crystals, m.p.: 157° C.

Analysis: $C_{14}H_{22}N_4$; Calculated: C 68.25, H 9.00, N 22.75; Observed: C 68.1, H 9.32, N 23.0.

EXAMPLE 7

α-Phenyl-β-[N,(2,2,6,6-tetramethyl-4-piperidinyl)]-aminoacrylonitrile 50 g (0.32 mole) of 2,2,6,6-tetramethyl-4-aminopiperidine, 46.4 g (0.32 mole) of formylphenyl acetonitrile and 0.8 g of glacial acetic acid were boiled under reflux for 1.5 hours in 400 ml of benzene over a water separator. After the solvent had been distilled off, the residue was recrystallised from isopropanol. Yield: 50 g of white crystals, m.p.: 149° C.

Analysis: $C_{18}H_{25}N_3$; Calculated: C 76.3, H 8.89, N 14.8; Observed: C 76.2, H 9.11, N 14.8.

EXAMPLE 8

Stabilisation of polystyrene 0.25% by weight of various compounds according to the invention were worked into polystyrene 168 N on a roll at a temperature of 135° C., and 1 mm thick test specimens were produced from the rough sheet thus obtained in a press at a temperature of 160° C.

The test specimens were artificially weathered in a xenon Weather-O-Meter (WOM) (sprinkling cycle 17:3; Pyrex filter). The spectral colour density Pc was determined as a measure of yellowing. The spectral colour density Pc is a colour value of the Helmholtz system and expresses colour intensity. The results are set out in Table 3.

Table 3

| Stabiliser Compound No. See Table 2 | Quantity % by weight | Pc | | |
|---|---|---|---|---|
| | | 0 h WOM | 1500 h WOM | 3000 h WOM |
| None | — | 0.020 | 0.17 | 0.31 |
| I | 0.25 | 0.019 | 0.049 | 0.19 |
| II | 0.25 | 0.019 | 0.052 | 0.20 |
| IV | 0.25 | 0.020 | 0.051 | 0.21 |
| IX | 0.25 | 0.019 | 0.048 | 0.17 |

EXAMPLE 9

Stabilisation of rigid PVC 100 parts of rigid PVC of the Vinnol H 60 D type were combined with 2 parts of the heat stabiliser Mark WSX and 0.25 part of one of the compounds according to the invention as identified in Table 2 on a roll at 170° C., homogenised and processed into 5 mm thick test specimens in a press at 170° C. These test specimens were subjected to artificial weathering in a xenon Weather-O-Meter (WOM) (sprinkling cycle 17:3; Pyrex filter). The spectral colour density Pc was determined as a measure of yellowing. The results are set out in Table 4.

Table 4

| Stabiliser compound No. see Table 2 | Quantity % by weight | Pc | | |
|---|---|---|---|---|
| | | 0 h | 1000 h | 2000 h WOM |
| none | — | 0.084 | 0.60 | 0.85 |
| I | 0.25 | 0.082 | 0.16 | 0.44 |
| II | 0.25 | 0.084 | 0.27 | 0.42 |
| IV | 0.25 | 0.071 | 0.16 | 0.35 |
| IX | 0.25 | 0.076 | 0.18 | 0.37 |

EXAMPLE 10

Stabilisation of ABS

High-impact ABS-graft polymer was compounded with 1% by weight of the compounds according to the invention, followed by the production of standard small test bars by injection moulding. The test specimens were weathered in a xenon Weather-O-Meter (WOM). After weathering periods of 200 hours and 500 hours, the impact strength values were determined under the conditions laid down in DIN 53 453.

The reduction in the impact strength values is a measure of the extent of the mechanical degradation of the polymer induced by weathering.

The results are set out in Table 5.

Table 5

| Stabiliser (compound No. see Table 2) | Quantity % (by weight) | $a_n$ after | |
|---|---|---|---|
| | | 200 h | 500 h WOM |
| none | — | 2.1 | — |
| I | 1 | 63 | 3.4 |
| II | 1 | 42 | 2.7 |
| VIII | 1 | 48 | 3.1 |

EXAMPLE 11

(a) Production specification for the polyurethane to be stabilised 800 parts of an adipic acid/1,6-hexane diol/2,2-dimethyl-1,3-propane diol mixed polyester (molar ratio of the glycols 65:35) with a molecular weight of 1910 are mixed with 15.8 parts of N-methyl-bis-(β-hydroxypropyl)-amine, 223.95 parts of dimethyl formamide, followed by heating for 50 minutes to 45°–50° C. After cooling to room temperature, the NCO-prepolymer formed has an NCO-content of 2.86% (based on solid substance).

600 parts of this prepolymer solution are introduced with stirring into a solution of 28.3 parts of $N_2N.NH.CO.NH.CH_2.CH_2.CO.NH.NH_2$ in 56 parts of water and 670 parts of dimethyl formamide.

The homogeneous viscous solution is pigmented with 4% of rutile, based on solids, further reacted with 2.0 parts of hexane diisocyanate and thereafter has a viscosity of 520 poises at 25° C.

(b) Measurement of the stabilising effect on elastomer films and (cut) filaments The elastomer solutions are homogenised by stirring with and without the stabilisers and comparison substances added in the quantities indicated (in the form of a concentrated solution in dimethyl formamide) and the resulting solution is processed into the shaped articles.

The solutions (c = 20%) are preferably coated onto glass plates in layer thicknesses of approximately 0.2 mm and dried in a drying cabinet at 70° to 100° C. to form films.

The films can be sliced by the screening test into strips approximately 1 cm wide and exposed to light in a Fadeometer (for assessment of discolouration and qualitative degradation behaviour during exposure).

The films are preferably sliced in a film slicing machine to form rectangular filaments with an overall denier of about 200 to 300 dtex and exposed to light in the form of these cut filaments. On account of the large surface, the damage caused by exposure is more intensive in this case and substantially equivalent to the behaviour of filaments produced on an industrial scale (by spinning processes). The solutions may also be wet or dry spun.

(c) Stabilisers added and stabilising effect

The quantities of stabiliser indicated are added to the polyurethane (urea) elastomer solutions a), the solutions are dried to form films and the films are exposed to light in a Fadeometer in the form of cut filaments and (partly) tested for tensile strength/elongation at break and discolouration (see Table a). The groups mentioned in the Examples (including comparison stabilisers and stabiliser-free substances) are in each case exposed at the same time in one Fadeometer.

Elastomer solutions containing 2% of stabiliser from Table 2 are spun into elastomer filaments both by dry spinning and by wet spinning, the elastomer filaments thus obtained showing substantially the same stabilisation (against discolouration and against deterioration in tensile strength) on exposure to UV-light as the filaments cut from films.

The additions produce a distinct increase in stabilisation both against deterioration in tensile strength and reduction of elongation at break and, in particular, against discolouration on exposure to light.

Compared with Ciba-Geigy's product "Tinuvin 770":

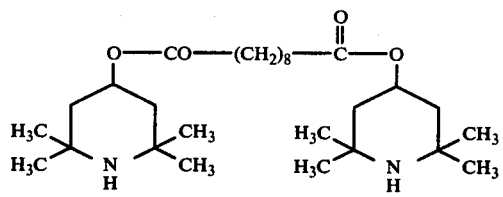

the stabilisers according to the invention show increased activity. Even when the quantity of stabiliser added is reduced to 0.5% by weight, substantially the same colour stabilisation is obtained.

Fadeometer exposure does the film containing stabiliser IX begin to show pale yellowish discolouration, whilst the film containing stabiliser VII is still substantially free from discolouration. All the films containing the stabilisers according to the invention do not show any signs of surface crazing on elongation after the exposure times indicated. In the hot water resistance test (1 hour at 95° C.), the films containing stabiliser IX, for example, show excellent resistance. Resistance to the effect of smoke gases and chlorine is improved by the stabilisers.

EXAMPLE 12

40 parts of dry ice ($CO_2$) are added to 10.7 parts of 99.0% ethylene diamine in 1350 parts of dimethyl formamide to form a fine carbamate suspension, into which 600 parts of the NCO-prepolymer solution produced in accordance with Example II a) are subsequently introduced over a period of 4 minutes. The solution is pigmented by the addition of 4% of $TiO_2$ (rutile), viscosity: 50 poises/20° C. The solution is then adjusted to a viscosity of 250 poises with 2.0 parts of hexane diisocyanate. The stabilisers are added to portions of the solutions, each dissolved in a little dimethyl formamide.

The elastomer films and sliced films are tested in the same way as described in the preceding Example. The Elongation at break and discoloration of cut filaments of polyester urethane elastomers (semicarbazido propionic acid hydrazide) with and without additions of stabiliser

| Stabiliser (Compound No. see Table 2) | Quantity of stabiliser added (based on solid substance) (%) | Tensile strength/elongation at break/discoloration/residual tensile strength (cN/dtex) (%) (in brackets; in %) after Fadeometer exposure for: | | | | |
|---|---|---|---|---|---|---|
| | | 0 | 22 | 44 | 66 | 88 | 123 hours |
| No stabiliser added | 0 | 0.67/680 colourless | — yellowish-yellow | 0.30/515 yellow (45) | 0.13/220 yellow-brown (19) | n.m. yellow-brown — | n.m. yellow-brown — |
| II | 2 | 0.59/675 colourless (100) | 0.56/645 colourless (95) | 0.55/630 almost colourless (93) | 0.46/610 almost colourless (71) | 0.41/595 almost colourless yellowish (70) | 0.39/545 yellowish (66) |
| Comparison with Tinuvin 770 | 2 | 0.63/675 colourless (100) | 0.56/570 colourless (90) | 0.50/625 almost colourless (78) | 0.45/575 almost colourless (71) | 0.42/550 yellowish (66) | 0.35/520 yellowish (55) |
| I | 2 | 0.65/670 colourless (100) | — colourless | 0.57/630 almost colourless (79) | — almost colourless | — almost colourless yellowish | — yellowish |
| IV | 2 | 0.57/670 colourless (100) | — colourless | 0.53/630 colourless (39) | — almost colourless | — almost colourless yellowish | — yellowish |

(n.m. = no longer measurable (tensile strength below 0.1 cm/dtex; elongation at break below 200%))

Other stabilisers (2% of each incorporated in the polyurethane) are tested by the screening test on strips of film. After Fadeometer exposure for 22, 44, 66 and 88 Fadeometer hours, the non-stabilised film strips are bright yellow in colour after only 44 hours and, on elongation, show surface crazing, whilst the films containing additions of stabilisers VI and IX (see Table 2) are colourless after 88 hours. Only after 154 hours' polyurethane chain-extended with ethylene diamine undergoes photodegradation to a far greater extent than the hydrazide-extended polyurethane according to Example 11. However, in this case as well, the stabilisers according to the invention produce distinct stabilisation of the polymer, the stabilising effect obtained being more favourable than that obtainable in cases where Tinuvin 770 is used.

Table 8

| | Fadeometer exposure of film strips | | | | | |
|---|---|---|---|---|---|---|
| | after 22 hours | 44 hours | 66 hours | 88 hours | 156 hours | 230 hours |
| No stabiliser added | yellow Film without any strength, crazing. Strength largely degraded | yellow (brown) Films without strength, totally degraded | yellow (brown) | yellow brown Films without strength, totally degraded | totally degraded | totally degraded dark brown |

Table 8-continued

| | Fadeometer exposure of film strips | | | | | |
|---|---|---|---|---|---|---|
| | after 22 hours | 44 hours | 66 hours | 88 hours | 156 hours | 230 hours |
| + 2% by weight of stabiliser, see Table 2 | colourless Strength substantially intact | colourless Substantially unchanged strength, no crazing, fully elastic | colourless | colourless fully elastic | colourless fully elastic | colourless, strength largely intact, no crazing |

EXAMPLE 13

400 parts of a polytetramethyl ether diol with a molecular weight of 1045 (Polymeg 1000, a product of the Quaker Oats Company) are reacted at 50° C. with a solution of 140.8 parts of diphenyl methane-4,4'-diisocyanate and 135 parts of dimethyl formamide until the NCO-content amounts to 3.2% (based on the solids content of the prepolymer solution).

6.02 parts of hydrazine hydrate are dissolved in 898 parts of dimethyl formamide, the carbonate suspension of the hydrazine is formed by the addition of 10 parts of dry ice and the suspension thus formed is reacted by stirring in 430 parts of the above NCO-prepolymer solution to form the segmented linear polyurethane. The homogeneous viscous elastomer solution (51 poises/20° C.) is pigmented with a $TiO_2$-suspension (4% $TiO_2$/rutile, based on elastomer solids).

Various portions of the solution are coated on to form elastomer films both with and without (comparison test) stabilisers added to them.

These elastomer films are exposed in a Fadeometer in the form of strips (for results, see Table 8). The results show that the unstabilised polyether urethane yellows very quickly and has been degraded after only 22 hours' Fadeometer exposure (no more strength, surface of film crazes with only slight elongation). By contrast, the stabilised film strip is still colourless and fully elastic, even after 156 hours' Fadeometer exposure.

$\beta$-cyanoethyl, $\beta$-alkoxycarbonylethyl having 1 to 3 carbon atoms in the alkoxy moiety, phenyl, phenyl substituted with alkyl having 1 to 4 carbon atoms, halogen or methoxy or

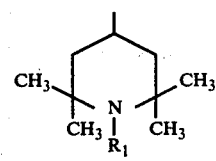

wherein $R_1$ is as aforesaid; $R_3$ is hydrogen, alkyl having 1 to 4 carbon atoms, phenyl or phenyl substituted with alkyl having 1 to 4 carbon atoms, halogen or methoxy; $R_4$ is —CN, —COOR$_6$,

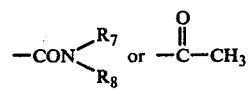

wherein $R_6$ is alkyl having 1 to 12 carbon atoms or cycloalkyl having 5 to 8 carbon atoms and $R_7$ and $R_8$, which may be the same or different, are hydrogen, alkyl having 1 to 12 carbon atoms, cycloalkyl having 5 to 8 carbon atoms, hydroxyalkyl having 1 to 4 carbon atoms or Tensile strength/elongation at break and discoloration of sliced filaments of polyester urethane elastomers (ethylene diamine chain extension) with and without stabilisers added

| Stabiliser (Compound No., see Table 2) | Quantity of stabiliser added (based on solid substance) (%) | Tensile strength/elongation at break/residual tensile strength (cN/dtex) (%) (in % - value in brackets) | | | | | |
|---|---|---|---|---|---|---|---|
| | | 0 | 22 | 44 | 66 | 88 | 123 hours |
| No stabiliser added | 0 | 0.56/650 (100) | 0.22/550 (39) | 0.17/4 5 (30) | n.m. — | n.m. — | n.m. — |
| Comparison with Tinuvin | 2 | 0.61/670 (100) | 0.35/575 (57) | 0.22/475 (36) | 0.12/390 (19) | n.m. — | n.m. — |
| Stabiliser II | 2 | 0.55/645 (100) | 0.42/614 (76) | 0.26/540 (47) | 0.21/490 (38) | 0.16/435 (29) | 0.11/320 (20) |
| Stabiliser IV | 2 | 0.55/650 (100) | 0.41/592 | 0.27/525 | 0.19/460 | 0.15/430 | 0.11/360 | n.m. = no longer measurable (tensile strength below 0.1 cm/dtex; elongation at break below 200%)

We claim:
1. A compound of the formula

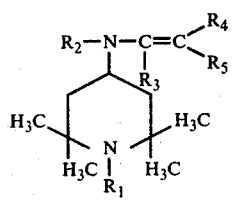

wherein $R_1$ is hydrogen or methyl; $R_2$ is hydrogen, alkyl having 1 to 8 carbon atoms, cycloalkyl having 5 to 8 carbon atoms, aralkyl having 7 to 12 carbon atoms,

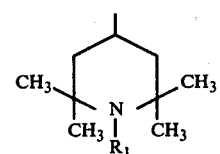

wherein $R_1$ is as aforesaid and $R_5$ is —CN, —COOR$_6$,

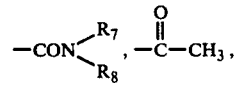

phenyl or phenyl substituted with alkyl having 1 to 4 carbon atoms, halogen or methoxy, $R_6$, $R_7$ and $R_8$ being as aforesaid.

2. The compound of claim 1 wherein $R_1$ is hydrogen, $R_2$ is hydrogen, alkyl having 1 to 8 carbon atoms, benzyl, cyclohexyl, phenyl, phenyl substituted with alkyl having 1 to 4 carbon atoms, halogen or methoxy or

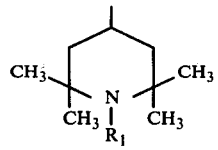

wherein $R_1$ is hydrogen; $R_3$ is hydrogen or methyl; $R_4$ is —CN, —COOR$_6$ or

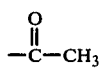

wherein $R_6$ is alkyl having 1 to 12 carbon atoms or cyclohexyl and $R_5$ is —CN, —COOR$_6$,

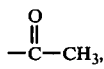

phenyl or phenyl substituted with alkyl having 1 to 4 carbon atoms, halogen or methoxy, $R_6$ being as aforesaid.

3. The compound of claim 1 wherein $R_1$ is hydrogen; $R_2$ is hydrogen, methyl, cyclohexyl or phenyl; $R_3$ is hydrogen or methyl; $R_4$ is —CH, —COOR$_6$ or

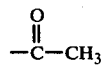

wherein $R_6$ is alkyl having 1 to 12 carbon atoms and $R_5$ is —CN, —COOR$_6$,

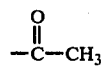

or phenyl, $R_6$ being as aforesaid.

4. A process for producing a compound of claim 1 wherein one equivalent of the compound of the formula

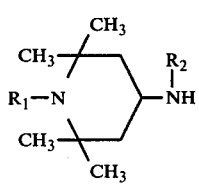

(III)

is reacted with 0.5 to 1.5 equivalents of a compound of the formula

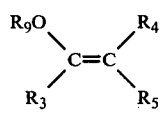

(IV)

at a temperature of from 0° to 100° C., $R_1$ being hydrogen or methyl; $R_2$ being hydrogen, alkyl having 1 to 8 carbon atoms, cycloalkyl having 5 to 8 carbon atoms, aralkyl having 7 to 12 carbon atoms, β-cyanoethyl, β-alkoxycarbonylethyl having 1 to 3 carbon atoms in the alkoxy moiety, phenyl, phenyl substituted with alkyl having 1 to 4 carbon atoms, halogen or methoxy or

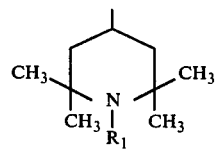

wherein $R_1$ is as aforesaid; $R_3$ being hydrogen, alkyl having 1 to 4 carbon atoms, phenyl, phenyl substituted with alkyl having 1 to 4 carbon atoms, halogen or methoxy; $R_4$ being —CN, —COOR$_6$,

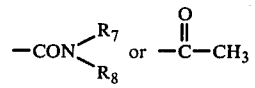

wherein $R_6$ is alkyl having 1 to 12 carbon atoms or cycloalkyl having 5 to 8 carbon atoms and $R_7$ and $R_8$, which may be the same or different, are hydrogen, alkyl having 1 to 12 carbon atoms, cycloalkyl having 5 to 8 carbon atoms, hydroxyalkyl having 1 to 4 carbon atoms or

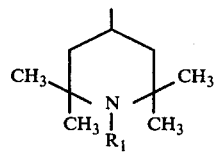

wherein $R_1$ is as aforesaid and $R_5$ is —CN, —COOR$_6$,

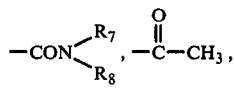

phenyl or phenyl substituted with alkyl having 1 to 4 carbon atoms, halogen or methoxy, $R_6$, $R_7$ and $R_8$ being as aforesaid, $R_9$ is hydrogen or alkyl having 1 to 4 carbon atoms.

5. The process of claim 4 wherein one equivalent of the compound of formula (III) is reacted with 0.8 to 1.2 equivalents of the compound of formula (IV).

6. A method of stabilizing a polymer which comprises adding to the polymer a stabilizing amount of a compound of claim 1.

7. The method of claim 6 wherein said compound is added in an amount of from 0.01 to 5% by weight, based on the weight of the polymer.

8. The method of claim 6 wherein said compound is added in an amount of from 0.1 to 3% by weight, based on the weight of the polymer.

9. The stabilized polymer of claim 6.

10. A compound obtainable by the process which comprises reacting one equivalent of a compound of the formula

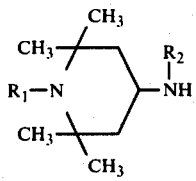

(III)

with 0.5 to 1.5 equivalents of a compound of the formula

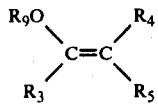

(IV)

at a temperature of from 0° to 100° C., $R_1$ being hydrogen or methyl; $R_2$ being hydrogen, alkyl having 1 to 8 carbon atoms, cycloalkyl having 5 to 8 carbon atoms, aralkyl having 7 to 12 carbon atoms, β-cyanoethyl, β-alkoxycarbonylethyl having 1 to 3 carbon atoms in the alkoxy moiety, phenyl, phenyl substituted with alkyl having 1 to 4 carbon atoms, halogen or methoxy or

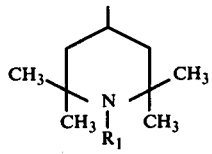

wherein $R_1$ is as aforesaid; $R_3$ being hydrogen, alkyl having 1 to 4 carbon atoms, phenyl, phenyl substituted with alkyl having 1 to 4 carbon atoms, halogen or methoxy; $R_4$ being —CN, —COOR$_6$,

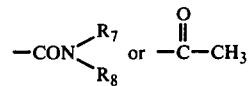

wherein $R_6$ is alkyl having 1 to 12 carbon atoms or cycloalkyl having 5 to 8 carbon atoms and $R_7$ and $R_8$, which may be the same or different, are hydrogen, alkyl having 1 to 12 carbon atoms, cycloalkyl having 5 to 8 carbon atoms, hydroxyalkyl having 1 to 4 carbon atoms or

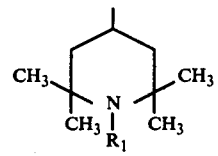

wherein $R_1$ is as aforesaid and $R_5$ is —CN, —COOR$_6$,

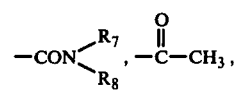

phenyl or phenyl substituted with alkyl having 1 to 4 carbon atoms, halogen or methoxy, $R_6$, $R_7$ and $R_8$ being as aforesaid, $R_9$ is hydrogen or alkyl having 1 to 4 carbon atoms.

* * * * *